United States Patent [19]

Muller et al.

[11] Patent Number: 5,635,517

[45] Date of Patent: Jun. 3, 1997

[54] METHOD OF REDUCING TNFα LEVELS WITH AMINO SUBSTITUTED 2-(2,6-DIOXOPIPERIDIN-3-YL)-1-OXO-AND 1,3-DIOXOISOINDOLINES

[75] Inventors: George W. Muller, Bridgewater; David I. Stirling, Branchburg; Roger S. -C. Chen, Edison, all of N.J.

[73] Assignee: Celgene Corporation, Warren, N.J.

[21] Appl. No.: 690,258

[22] Filed: Jul. 24, 1996

[51] Int. Cl.$^6$ .................. A61K 31/445; C07D 401/04
[52] U.S. Cl. ............................. 514/323; 546/201
[58] Field of Search ................... 546/201; 514/323, 514/231.5, 231.2, 327

[56] References Cited

U.S. PATENT DOCUMENTS 5,385,901  1/1995  Kaplan et al. .............. 514/231.5
5,463,083  10/1995  Muller ....................... 546/201

OTHER PUBLICATIONS

N. Ake Jonsson, Chemical Structure and Teratogenic Properties: A Review Of Available Data On Structure–Activity Relationships and Mechanism Of Action Of Thalidomide Analogues, *Acta Pharm. Suicica*, vol. 9, pp. 521–542 (1972).

H. Koch, The Arene Oxide Hypothesis Of Thalidomide Action. Considerations On the Molecular Mechanism Of Action Of the Classical Teratogen, *Sci. Pharm.*, vol. 49, pp. 67–99 (1981).

L. Sekut et al., Pathophysiology and Regulation Of TNF–α In Inflammation, DN&P 9(5), pp. 261–269, (1996).

Smith, R.L.; Fabro, S.; Schumacher, H. and William, R.T.; Studies on the relationship between the Chemical Structured and Embryotoxic Activity Of Thalidomide and Related Compounds. A Symposium on Embryotoxic Activity of dough, edited by Pobinson, J.M. et al. 1965, pp. 194–209. See p. 202, Table 6.

*Primary Examiner*—C. Warren Ivy
*Assistant Examiner*—C. S. Aulakh
*Attorney, Agent, or Firm*—Mathews, Collins, Shepherd & Gould, P.A.

[57] ABSTRACT

1-Oxo- and 1,3-dioxo-2-(2,6-dioxopiperidin-3-yl) isoindolines substituted with amino in the benzo ring reduce the levels of TNFα in a mammal. A typical embodiment is 1,3-dioxo-2-(2,6-dioxopiperidin-3-yl)-5-aminoisoindoline.

10 Claims, No Drawings

METHOD OF REDUCING TNFα LEVELS WITH AMINO SUBSTITUTED 2-(2,6-DIOXOPIPERIDIN-3-YL)-1-OXO-AND 1,3-DIOXOISOINDOLINES

The present invention relates a method of reducing levels of tumor necrosis factor α in a mammal through the administration of an amino substituted 2-(2,6-dioxopiperidin-3-yl)-1-oxoisoindolines and 1,3-dioxoisoindolines and to pharmaceutical compositions of such amino substituted indoline derivatives.

BACKGROUND OF THE INVENTION

Tumor necrosis factor α, or TNFα, is a cytokine which is released primarily by mononuclear phagocytes in response to a number immunostimulators. When administered to animals or humans, it causes inflammation, fever, cardiovascular effects, hemorrhage, coagulation, and acute phase responses similar to those seen during acute infections and shock states. Excessive or unregulated TNFα production thus has been implicated in a number of disease conditions. These include endotoxemia and/or toxic shock syndrome {Tracey et al., *Nature* 330, 662–664 (1987) and Hinshaw et al., *Circ. Shock* 30, 279–292 (1990)}; cachexia {Dezube et al., *Lancet*, 335 (8690), 662 (1990)} and Adult Respiratory Distress Syndrome where TNFα concentration in excess of 12,000 pg/mL have been detected in pulmonary aspirates from ARDS patients {Millar et al., *Lancet* 2(8665), 712–714 (1989)}. Systemic infusion of recombinant TNFα also resulted in changes typically seen in ARDS {Ferrai-Baliviera et al., *Arch. Surg.* 124(12), 1400–1405 (1989)}.

TNFα appears to be involved in bone resorption diseases, including arthritis. When activated, leukocytes will produce bone-resorption, an activity to which the data suggest TNFα contributes. {Bertolini et al., *Nature* 319, 516–518 (1986) and Johnson et al., *Endocrinology* 124(3), 1424–1427 (1989).} TNFα also has been shown to stimulate bone resorption and inhibit bone formation in vitro and in vivo through stimulation of osteoclast formation and activation combined with inhibition of osteoblast function. Although TNFα may be involved in many bone resorption diseases, including arthritis, the most compelling link with disease is the association between production of TNFα by tumor or host tissues and malignancy associated hypercalcemia {*Calci. Tissue Int.* (US) 46(Suppl.), S3–10 (1990)}. In Graft versus Host Reaction, increased serum TNFα levels have been associated with major complication following acute allogenic bone marrow transplants {Holler et al., *Blood*, 75(4), 1011–1016 (1990)}.

Cerebral malaria is a lethal hyperacute neurological syndrome associated with high blood levels of TNFα and the most severe complication occurring in malaria patients. Levels of serum TNFα correlated directly with the severity of disease and the prognosis in patients with acute malaria attacks {Grau et al., *N. Engl. J. Med.* 320(24), 1586–1591 (1989)}.

TNFα also plays a role in the area of chronic pulmonary inflammatory diseases. The deposition of silica particles leads to silicosis, a disease of progressive respiratory failure caused by a fibrotic reaction. Antibody to TNFα completely blocked the silica-induced lung fibrosis in mice {Pignet et al., *Nature*, 344:245–247 (1990)}. High levels of TNFα production (in the serum and in isolated macrophages) have been demonstrated in animal models of silica and asbestos induced fibrosis {Bissonnette et al., *Inflammation* 13(3), 329–339 (1989)}. Alveolar macrophages from pulmonary sarcoidosis patients have also been found to spontaneously release massive quantities of TNFα as compared with macrophages from normal donors {Baughman et al., *J. Lab. Clin. Med.* 115(1), 36–42 (1990)}.

TNFα is also implicated in the inflammatory response which follows reperfusion, called reperfusion injury, and is a major cause of tissue damage after loss of blood flow {Vedder et al., *PNAS* 87, 2643–2646 (1990)}. TNFα also alters the properties of endothelial cells and has various pro-coagulant activities, such as producing an increase in tissue factor pro-coagulant activity and suppression of the anticoagulant protein C pathway as well as down-regulating the expression of thrombomodulin {Sherry et al., *J. Cell Biol.* 107, 1269–1277 (1988)}. TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells {Munro et al., *Am. J. Path.* 135(1), 121–132 (1989)}.

Moreover, it now is known that TNFα is a potent activator of retrovirus replication including activation of HIV-1. {Duh et al., *Proc. Nat. Acad. Sci.* 86, 5974–5978 (1989); Poll et al., *Proc. Nat. Acad. Sci.* 87, 782–785 (1990); Monto et al., *Blood* 79, 2670 (1990); Clouse et al., *J. Immunol.* 142, 431–438 (1989); Poll et al., *AIDS Res. Hum. Retrovirus*, 191–197 (1992)}. AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T lymphocyte activation. Therefore, interference with cytokine activity such as by prevention or inhibition of cytokine production, notably TNFα, in an HIV-infected individual assists in limiting the maintenance of T lymphocyte caused by HIV infection.

Monocytes, macrophages, and related cells, such as kupffer and glial cells, also have been implicated in maintenance of the HIV infection. These cells, like T cells, are targets for viral replication and the level of viral replication is dependent upon the activation state of the cells. {Rosenberg et al., *The Immunopathogenesis of HIV Infection*, Advances in Immunology, 57 (1989)}. Cytokines, such as TNFα, have been shown to activate HIV replication in monocytes and/or macrophages {Poli et al. *Proc. Natl. Acad. Sci.*, 87, 782–784 (1990)}, therefore, prevention or inhibition of cytokine production or activity aids in limiting HIV progression for T cells. Additional studies have identified TNFα as a common factor in the activation of HIV in vitro and has provided a clear mechanism of action via a nuclear regulatory protein found in the cytoplasm of cells (Osborn, et al., *PNAS* 86 2336–2340). This evidence suggests that a reduction of TNFα synthesis may have an antiviral effect in HIV infections, by reducing the transcription and thus virus production.

AIDS viral replication of latent HIV in T cell and macrophage lines can be induced by TNFα {Folks et al., PNAS 86, 2365–2368 (1989)}. A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) {Osborn et al., PNAS 86, 2336–2340 (1989)}. TNFα in AIDS associated cachexia is suggested by elevated serum TNFα and high levels of spontaneous TNFα production in peripheral blood monocytes from patients {Wright et al. J. Immunol. 141(1), 99–104 (1988)}. TNFα has been implicated in various roles with other viral infections, such as the cytomegalia virus (CMV), influenza virus, adenovirus, and the herpes family of viruses for similar reasons as those noted.

The nuclear factor κB (NFκB) is a pleiotropic transcriptional activator (Lenardo, et al. Cell 1989, 58, 227–29). NFκB has been implicated as a transcriptional activator in a variety of disease and inflammatory states and is thought to regulate cytokine levels including but not limited to TNFα and also to be an activator of HIV transcription (Dbaibo, et al. J. Biol. Chem. 1993, 17762–66; Duh et al. Proc. Natl. Acad. Sci. 1989, 86, 5974–78; Bachelerie et al. Nature 1991, 350, 709–12; Boswas et al. J. Acquired Immune Deficiency Syndrome 1993, 6, 778–786; Suzuki et al. Biochem. And Biophys. Res. Comm. 1993, 193, 277–83; Suzuki et al. Biochem. And Biophys. Res Comm. 1992, 189, 1709–15; Suzuki et al. Biochem. Mol. Bio. Int. 1993, 31(4), 693–700; Shakhov et al. Proc. Natl. Acad. Sci. USA 1990, 171, 35–47; and Staal et al. Proc. Natl. Acad. Sci. USA 1990, 87, 9943–47). Thus, inhibition of NFκB binding can regulate transcription of cytokine gene(s) and through this modulation and other mechanisms be useful in the inhibition of a multitude of disease states. The compounds described herein can inhibit the action of NFκB in the nucleus and thus are useful in the treatment of a variety of diseases including but not limited to rheumatoid arthritis, rheumatoid spondylitis, osteoarthritis, other arthritic conditions, septic shock, septis, endotoxic shock, graft versus host disease, wasting, Crohn's disease, ulcerative colitis, multiple sclerosis, systemic lupus erythrematosis, ENL in leprosy, HIV, AIDS, and opportunistic infections in AIDS. TNFα and NFκB levels are influenced by a reciprocal feedback loop. As noted above, the compounds of the present invention affect the levels of both TNFα and NFκB.

Many cellular functions are mediated by levels of adenosine 3',5'-cyclic monophosphate (cAMP). Such cellular functions can contribute to inflammatory conditions and diseases including asthma, inflammation, and other conditions (Lowe and Cheng, Drugs of the Future, 17(9), 799–807, 1992). It has been shown that the elevation of cAMP in inflammatory leukocytes inhibits their activation and the subsequent release of inflammatory mediators, including TNFα and NFκB. Increased levels of cAMP also leads to the relaxation of airway smooth muscle.

Decreasing TNFα levels and/or increasing cAMP levels thus constitutes a valuable therapeutic strategy for the treatment of many inflammatory, infectious, immunological or malignant diseases. These include but are not restricted to septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, Crohn's disease, ulcerative colitis, multiple sclerosis, systemic lupus erythrematosis, ENL in leprosy, radiation damage, and hyperoxic alveolar injury. Prior efforts directed to the suppression of the effects of TNFα have ranged from the utilization of steroids such as dexamethasone and prednisolone to the use of both polyclonal and monoclonal antibodies {Beutler et al., Science 234, 470–474 (1985); WO 92/11383}.

DETAILED DESCRIPTION

The present invention is based on the discovery that a class of non-polypeptide compounds more fully described herein decrease the levels of TNFα and elevate the levels of adenosine 3',5'-cyclic monophosphate.

In particular, the invention pertains to the method of reducing undesirable levels of TNFα in a mammal by administering to the mammal an effective amount of a compound of the formula:

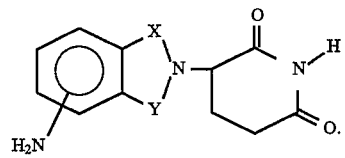

in which one of X and Y is C=O and the other of X and Y is C=O or $CH_2$

The compounds of Formula I are used, under the supervision of qualified professionals, to inhibit the undesirable effects of TNFα. The compounds can be administered orally, rectally, or parenterally, alone or in combination with other therapeutic agents including antibiotics, steroids, etc., to a mammal in need of treatment.

The compounds of the present invention also can be used topically in the treatment or prophylaxis of topical disease states mediated or exacerbated by excessive TNFα production, respectively, such as viral infections, such as those caused by the herpes viruses, or viral conjunctivitis, etc.

The compounds also can be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

Certain of these compounds, such as 1,3-dioxo-2-(2,6-dioxopiperidin-3-yl)-4-aminoisoindoline and 1,3-dioxo-2-(2,6-dioxopiperidin-3-yl)-5-aminoisoindoline are known. See, e.g., Jönsson, Acta Pharma. Succica, 9, 521–542 (1972).

In any event, the compounds can be prepared using methods which are known in general. In particular, the compounds can be prepared through catalytic hydrogenation of the corresponding nitro compound.

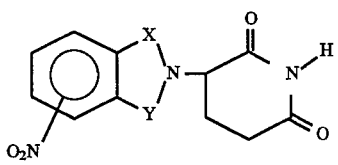

The nitro intermediates of Formula II are known or can be obtained though conventional processes. For example, a nitrophthalic anhydride is allowed to react with α-aminoglutarimide hydrochloride {alternatively named as 2,6-dioxopiperidin-3-ylammonium chloride} in the presence of sodium acetate and glacial acetic acid to yield an intermediate of Formula II in which X and Y are both C=O.

In a second route, a lower alkyl ester of nitro-ortho-toluic acid is brominated with N-bromosuccinimide under the influence of light to yield a lower alkyl 2-(bromomethyl) nitrobenzoate. This is allowed to react with 2,6-dioxopiperidin-3-ammonium chloride in, for example, dimethylformamide in the presence of triethylamine to yield an intermediate of Formula II in which one of X is C=O and the other is $CH_2$.

The compounds of Formula I possess a center of chirality and can exist as optical isomers. Both the racemates of these isomers and the individual isomers themselves, as well as diastereomers when there are two chiral centers, are within the scope of the present invention. The racemates can be used as such or can be separated into their individual isomers mechanically as by chromatography using a chiral absorbant. Alternatively, the individual isomers can be prepared in chiral form or separated chemically from a mixture by forming salts with a chiral acid, such as the individual enantiomers of 10-camphorsulfonic acid, camphoric acid, α-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as obtain either or both substantially free of the other; i.e., in a form having an optical purity of >95%.

Alternatively, the compounds can be stereopreferentially synthesized by allowing the lower alkyl 2-(bromomethyl) nitrobenzoate intermediate discussed above to react with either (R)-1-benzyloxy-2,6-dioxo-3-tert.-butoxycarbonylaminopiperidine or (S)-1-benzyloxy-2,6-dioxo-3-tert.-butoxycarbonylaminopiperidine analogous to the method described by Robin et al., *Tetrahedron Asymmetry*, 6, 1249 (1995). Hydrogenation in this case not only reduces the nitro group to an amino group but also converts the N-benzyloxy group to an N-hydroxy group which can be removed with bromoacetophenone triethylamine and dimethylaminopyridine to yield the corresponding (R) or (S) enantiomer of Formula I.

The present invention also pertains to the physiologically acceptable non-toxic acid addition salts of the compounds of Formula I. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

Oral dosage forms include tablets, capsules, dragees, and similar shaped, compressed pharmaceutical forms containing from 1 to 100 mg of drug per unit dosage. Isotonic saline solutions containing from 20 to 100 mg/mL can be used for parenteral administration which includes intramuscular, intrathecal, intravenous and intra-arterial routes of administration. Rectal administration can be effected through the use of suppositories formulated from conventional carriers such as cocoa butter.

Pharmaceutical compositions thus comprise one or more compounds of Formula I associated with at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient. The compositions can be formulated so as to provide an immediate, sustained or delayed release of active ingredient after administration to the patient by employing procedures well known in the art.

Oral dosage forms include tablets, capsules, dragees, and similar shaped, compressed pharmaceutical forms containing from 1 to 100 mg of drug per unit dosage. Isotonic saline solutions containing from 20 to 100 mg/mL can be used for parenteral administration which includes intramuscular, intrathecal, intravenous and intra-arterial routes of administration. Rectal administration can be effected through the use of suppositories formulated from conventional carriers such as cocoa butter.

Pharmaceutical compositions thus comprise one or more compounds of Formula I associated with at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient. The compositions can be formulated so as to provide an immediate, sustained or delayed release of active ingredient after administration to the patient by employing procedures well known in the art.

Specific compounds falling within Formula I include 1-oxo-2-(2,6-dioxopiperidin-3-yl)-5-aminoisoindoline, 1-oxo-2-(2,6-dioxopiperidin-3-yl)-4-aminoisoindoline, 1-oxo-2-(2,6-dioxopiperidin-3-yl)-6-aminoisoindoline, 1-oxo-2-(2,6-dioxopiperidin-3-yl)-7-aminoisoindoline, 1,3-dioxo-2-(2,6-dioxopiperidin-3-yl)-4-aminoisoindoline, and 1,3-dioxo-2-(2,6-dioxopiperidin-3 -yl)-5-aminoisoindoline.

The following examples will serve to further typify the nature of this invention but should not be construed as a limitation in the scope thereof, which scope is defined solely by the appended claims.

EXAMPLE 1

A mixture of 1,3-dioxo-2-(2,6-dioxopiperidin-3-yl)-5-nitroisoindoline {alternatively named as N-(2,6-dioxopiperidin-3-yl)-4-nitrophthalimide} (1 g, 3.3 mmol) and 10% Pd/C (0.13 g) in 1,4-dioxane (200 mL) was hydrogenated at 50 psi for 6.5 hours. The catalyst was filtered through Celite and the filtrate concentrated in vacuo. The residue was crystallized from ethyl acetate (20 mL) to give 0.62 g (69%) of 1,3-dioxo-2-(2,6-dioxopiperidin-3-yl) -5-aminoisoindoline {alternatively named as N-(2,6-dioxopiperidin-3-yl)-4-aminophthalimide} as an orange solid. Recrystallization from dioxane/ethyl acetate gave 0.32 g of yellow solid: mp 318.5°–320.5° C.; HPLC (nova Pak C18,15/85 acetonitrile/0.1%$H_3PO_4$) 3.97 min (98.22%); $^1H$ NMR (DMSO-$d_6$) δ 11.08(s, 1H), 7.53–7.50 (d, J=8.3 Hz, 1H), 6.94(s, 1H), 6.84–6.81(d, J=8.3 Hz, 1H), 6.55(s,2H), 5.05–4.98(m, 1H), 2.87–1.99(m, 4H); $^{13}C$ NMR (DMSO-$d_6$) δ 172.79,170.16, 167.65, 167.14, 155.23, 134.21, 125.22, 116.92, 116.17, 107.05, 48.58, 30.97, 22.22; Anal. Calcd for $C_{13}H_{11}N_3O_4$: C, 57.14; H, 4.06; N, 15.38. Found: C, 56.52- H, 4.17; N, 14.60.

In a similar fashion from 1-oxo-2-(2,6-dioxopiperidin-3-yl)-5-nitroisoindoline, 1-oxo-2-(2,6-dioxopiperidin-3-yl)-4-nitroisoindoline, 1-oxo-2-(2,6-dioxopiperidin-3-yl)-6-nitroisoindoline, 1-oxo-2-(2,6-dioxopiperidin-3-yl)-7-nitroisoindoline, and 1,3-dioxo-2-(2,6-dioxopiperidin-3-yl)-4-nitroisoindoline, there is respectively obtained 1-oxo-2-(2,6-dioxopiperidin-3-yl)-5-aminoisoindoline, 1-oxo-2-(2,6-dioxopiperidin-3-yl)-4-aminoisoindoline, 1-oxo-2-(2,6-dioxopiperidin-3-yl)-6-aminoisoindoline, 1-oxo-2-(2,6-dioxopiperidin-3-yl)-7-aminoisoindoline, and 1,3-dioxo-2-(2,6-dioxopiperidin-3-yl)-4-aminoisoindoline, respectively, upon hydrogenation.

EXAMPLE 2

A mixture of 4-nitrophthalic anhydride (1.7 g, 8.5 mmol), α-aminoglutarimide hydrochloride (1.4 g, 8.5 mmol) and sodium acetate (0.7 g, 8.6 mmol) in glacial acetic acid (30 mL) was heated under reflux for 17 hours. The mixture was concentrated in vacuo and the residue was stirred with methylene chloride (40 mL) and water (30 mL). The aqueous layer was separated, extracted with methylene chloride (2×40 mL). The combined methylene chloride solutions were dried over magnesium sulfate and concentrated in vacuo to give 1.4 g (54%) of 1,3-dioxo-2-(2,6-dioxopiperidin-3-yl)-5-nitroisoindoline as a light brown solid. An analytical sample was obtained by recrystallization from methanol: mp 228.5°–229.5° C.; $^1H$ NMR (DMSO-$d_6$) δ 11.18(s, 1 H), 8.69–8.65(d,d J=1.9 and 8.0 Hz, 1H), 8.56(d, J=1.9 Hz, 1H), 8.21(d, H=8.2 Hz, 1H), 5.28(d,d J=5.3 and 12.8 Hz, 1H), 2.93–2.07(m, 4H); $^{13}C$ NMR (DMSO-$d_6$) δ 172.66, 169.47, 165.50, 165.23, 151.69, 135.70, 132.50, 130.05, 124.97, 118.34, 49.46, 30.85, 21.79; Anal. Calcd for $C_{13}H_9N_3O_6$: C, 51.49; H, 2.99; N, 13.86. Found: C, 51.59; H, 3.07; N, 13.73.

1-Oxo-2-(2,6-dioxopiperidin-3-yl)-5-nitroisoindoline, 1-oxo-2-(2,6-dioxopiperidin-3-yl)-4-nitroisoindoline, 1-oxo-2-(2,6-dioxopiperidin-3-yl)-6-nitroisoindoline, and 1-oxo-2-(2,6-dioxopiperidin-3-yl)-7-nitroisoindoline can be obtained by allowing 2,6-dioxopiperidin-3-ammonium chloride to react with methyl 2-bromomethyl-5-nitrobenzoate, methyl 2-bromomethyl-4-nitrobenzoate, methyl 2-bromomethyl-6-nitrobenzoate, and methyl 2-bromomethyl-7-nitrobenzoate, respectively, in dimethylformamide in the presence of triethylamine. The methyl 2-(bromomethyl)nitrobenzoates in turn are obtained from the corresponding methyl esters of nitro-ortho-toluic acids by conventional bromination with N-bromosuccinimide under the influence of light.

EXAMPLE 3

Tablets, each containing 50 mg of 1,3-dioxo-2-(2,6-dioxopiperidin-3-yl)-5-aminoisoindoline, can be prepared in the following manner:

| Constituents (for 1000 tablets) | |
|---|---|
| 1,3-dioxo-2-(2,6-dioxo-piperidin-3-yl)-5-amino-isoindoline | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralized water | q.s. |

The solid ingredients are first forced through a sieve of 0.6 mm mesh width. The active ingredient, lactose, talc, magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 4

Tablets, each containing 100 mg of 1,3-dioxo-2-(2,6-dioxopiperidin-3-yl)-5-aminoisoindoline, can be prepared in the following manner:

| Constituents (for 1000 tablets) | |
|---|---|
| 1,3-dioxo-2-(2,6-dioxo-piperidin-3-yl)-5-amino-isoindoline | 100.0 g |

-continued

| Constituents (for 1000 tablets) | |
|---|---|
| lactose | 100.0 g |
| wheat starch | 47.0 g |
| magnesium stearate | 3.0 g |

All the solid ingredients are first forced through a sieve of 0.6 mm mesh width. The active ingredient, lactose, magnesium stearate and half of the starch then are mixed. The other half of the starch is suspended in 40 mL of water and this suspension is added to 100 mL of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 5

Tablets for chewing, each containing 75 mg of 1-oxo-2-(2,6-dioxopiperidin-3-yl)-4-aminoisoindoline, can be prepared in the following manner:

| Composition (for 1000 tablets) | |
|---|---|
| 1-oxo-2-(2,6-dioxo-piperidin-3-yl)-4-amino-isoindoline | 75.0 g |
| mannitol | 230.0 g |
| lactose | 150.0 g |
| talc | 21.0 g |
| glycine | 12.5 g |
| stearic acid | 10.0 g |
| saccharin | 1.5 g |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. 1-Oxo-2-(2,6-dioxopiperidin-3-yl)-4-aminoisoindoline, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

EXAMPLE 6

Tablets, each containing 10 mg of 1-oxo-2-(2,6-dioxopiperidin-3-yl)-5-aminoisoindoline, can be prepared in the following manner:

| Composition (for 1000 tablets) | |
|---|---|
| 1-oxo-2-(2,6-dioxo-piperidin-3-yl)-5-amino-isoindoline | 10.0 g |
| lactose | 328.5 g |
| corn starch | 17.5 g |
| polyethylene glycol 6000 | 5.0 g |
| talc | 25.0 g |
| magnesium stearate | 4.0 g |
| demineralized water | q.s. |

The solid ingredients are first forced through a sieve of 0.6 mm mesh width. Then the active imide ingredient, lactose, talc, magnesium stearate and half of the starch are intimately mixed. The other half of the starch is suspended in 65 mL of water and this suspension is added to a boiling solution of the polyethylene glycol in 260 mL of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 7

Gelatin dry-filled capsules, each containing 100 mg of 1-oxo-2-(2,6-dioxopiperidin-3-yl)-6-aminoisoindoline, can be prepared in the following manner:

| Composition (for 1000 capsules) | |
|---|---|
| 1-oxo-2-(2,6-dioxo-piperidin-3-yl)-6-amino-isoindoline | 100.0 g |
| microcrystalline cellulose | 30.0 g |
| sodium lauryl sulfate | 2.0 g |
| magnesium stearate | 8.0 g |

The sodium lauryl sulfate is sieved into the 1-oxo-2-(2,6-dioxopiperidin-3-yl)-6-aminoisoindoline through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

EXAMPLE 8

A 0.2% injection or infusion solution can be prepared, for example, in the following manner:

| | |
|---|---|
| 1-oxo-2-(2,6-dioxo-piperidin-3-yl)-7-amino-isoindoline | 5.0 g |
| sodium chloride | 22.5 g |
| phosphate buffer pH 7.4 | 300.0 g |
| demineralized water | to 2500.0 mL |

1-Oxo-2-(2,6-dioxopiperidin-3-yl)-7-aminoisoindoline is dissolved in 1000 mL of water and filtered through a microfilter. The buffer solution is added and the whole is made up to 2500 mL with water. To prepare dosage unit forms, portions of 1.0 or 2.5 mL each are introduced into glass ampoules (each containing respectively 2.0 or 5.0 mg of imide).

What is claimed is:

1. The method of reducing undesirable levels of TNFα in a mammal which comprises administering thereto an effective amount of a compound of the formula:

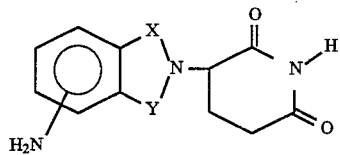

in which in said compound one of X and Y is C=O and the other of X and Y is C=O or CH₂.

2. The method according to claim 1 in which X is C=O and Y is CH₂.

3. The method according to claim 2 in which said compound is 1-oxo-2-(2,6-dioxopiperidin-3-yl)-5-aminoisoindoline.

4. The method according to claim 2 in which said compound is 1-oxo-2-(2,6-dioxopiperidin-3 -yl)-4-aminoisoindoline.

5. The method according to claim 2 in which said compound is 1-oxo-2-(2,6-dioxopiperidin-3 -yl)-6-aminoisoindoline.

6. The method according to claim 2 in which said compound is 1-oxo-2-(2,6-dioxopiperidin-3 -yl)-7-aminoisoindoline.

7. The method according to claim 1 in which each of X and Y is C=O.

8. The method according to claim 7 in which said compound is 1,3-dioxo-2-(2,6-dioxopiperidin-3-yl)-4-aminoisoindoline.

9. The method according to claim 7 in which said compound is 1,3-dioxo-2-(2,6-dioxopiperidin-3-yl)-5-aminoisoindoline.

10. A compound selected from the group consisting of 1-oxo-2-(2,6-dioxopiperidin-3-yl)-5-aminoisoindoline, 1-oxo-2-(2,6-dioxopiperidin-3-yl)-4-aminoisoindoline, 1-oxo-2-(2,6-dioxopiperidin-3-yl)-6-aminoisoindoline, and 1-oxo-2-(2,6-dioxopiperidin-3-yl)-7-aminoisoindoline.

* * * * *

REEXAMINATION CERTIFICATE (3797th)
United States Patent [19]

Muller et al.

[11] B 5,635,517

[45] Certificate Issued Jun. 29, 1999

[54] METHOD OF REDUCING TNFα LEVELS WITH AMINO SUBSTITUTED 2-(2,6-DIOXOPIPERIDIN-3-YL)-1-OXO-AND 1,3 DIOXOISOINDOLINES

[75] Inventors: George W. Muller, Bridgewater; David I. Stirling, Branchburg; Roger S.-C. Chen, Edison, all of N.J.

[73] Assignee: Celgene Corporation, Warren, N.J.

Reexamination Request:
No. 90/005,157, Apr. 20, 1998

Reexamination Certificate for:
Patent No.: 5,635,517
Issued: Jun. 3, 1997
Appl. No.: 08/690,258
Filed: Jul. 24, 1996

[51] Int. Cl.⁶ ........................ A61K 31/445; C07D 401/04
[52] U.S. Cl. ............................................. 514/323; 546/201
[58] Field of Search ........................... 514/323; 546/201

[56] References Cited

U.S. PATENT DOCUMENTS

| | | | |
|---|---|---|---|
| 4,808,402 | 2/1989 | Leibovich et al. | 424/423 |
| 5,593,990 | 1/1997 | D'Amato | 514/235.2 |
| 5,629,327 | 5/1997 | D'Amato | 514/323 |
| 5,712,291 | 1/1998 | D'Amato | 514/323 |

OTHER PUBLICATIONS

Leibovich et al, Macrophage–Induced Angiogensesis is Mediated by Tumor Necrosis Factor–α, *Letters To Nature*, vol. 329, Oct. 15, 1997, pp. 630–632.

*Primary Examiner*—Alan L. Rotman

[57] ABSTRACT

1-Oxo- and 1,3-dioxo-2-(2,6-dioxopiperidin-3-yl) isoindolines substituted with amino in the benzo ring reduce the levels of TNFα in a mammal. A typical embodiment is 1,3-dioxo-2(2,6-dioxopiperidin-3-yl)-5-aminoisoindoline.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–10 is confirmed.

* * * * *